US007001353B2

(12) United States Patent
Bosetto et al.

(10) Patent No.: US 7,001,353 B2
(45) Date of Patent: Feb. 21, 2006

(54) DEVICE AND A METHOD FOR DETERMINING BLOOD RECIRCULATION IN A VASCULAR ACCESS

(75) Inventors: Antonio Bosetto, Mirandola (IT); Francesco Paolini, Modena (IT)

(73) Assignee: Gambro Hospal (Scweiz) AG, Basel (CH)

( * ) Notice: Subject to any disclaimer, the term of this patent is extended or adjusted under 35 U.S.C. 154(b) by 756 days.

(21) Appl. No.: 09/913,857

(22) PCT Filed: Dec. 18, 2000

(86) PCT No.: PCT/IB00/01895

§ 371 (c)(1),
(2), (4) Date: Dec. 12, 2001

(87) PCT Pub. No.: WO01/45770

PCT Pub. Date: Jun. 28, 2001

(65) Prior Publication Data

US 2004/0073153 A1    Apr. 15, 2004

(30) Foreign Application Priority Data

Dec. 21, 1999  (IT) .............................. TO99A1138

(51) Int. Cl.
*A61M 37/00*  (2006.01)
*A61M 1/14*   (2006.01)
*B01D 11/00*  (2006.01)
*C02F 1/00*   (2006.01)

(52) U.S. Cl. ...................... 604/5.01; 422/44; 210/646; 210/739

(58) Field of Classification Search ............... 604/4.01, 604/5.01–5.04, 6.09, 6.11, 6.01, 6.16, 8, 19, 604/28, 65; 210/650.651, 645–647, 739, 210/745, 746, 85, 87, 97, 805, 94, 96.1, 96.2, 210/138, 139, 321.71, 321.6; 600/504, 366, 600/368–370, 454; 422/44, 82.09; 128/898; 73/861.07, 861.08, 861.11
See application file for complete search history.

(56) References Cited

U.S. PATENT DOCUMENTS

| | | | |
|---|---|---|---|
| 5,507,723 A * | 4/1996 | Keshaviah | 604/6.11 |
| 5,588,959 A | 12/1996 | Ahmad et al. | |
| 5,595,182 A * | 1/1997 | Krivitski | 600/505 |
| 5,866,015 A * | 2/1999 | Kramer | 210/739 |
| 6,210,591 B1 * | 4/2001 | Krivitski | 210/739 |

(Continued)

FOREIGN PATENT DOCUMENTS

EP    0 693 297 A1 *  1/1996

(Continued)

*Primary Examiner*—Patricia Bianco
(74) *Attorney, Agent, or Firm*—Finnegan, Henderson, Farabow, Garrett & Dunner L.L.P.

(57) ABSTRACT

A method is described for determining recirculation of blood in a vascular access of a patient undergoing dialysis treatment using a dialysis machine with an arterial line for withdrawing blood from the patient's body, a dialysis filter, and a venous line for returning blood to the patient's body. The method induces a disturbance in the blood flowing in the venous line. The disturbance is of a magnitude capable of bringing the system into a transient state and determining blood recirculation in the vascular access during the transient state as a function of the magnitude of the disturbance induced in the arterial line. In particular, the disturbance relates to the variation of the hemoglobin concentration in the blood flowing in the venous line. The variation is caused by controlling a change in the ultrafiltration flow in the dialysis filter.

6 Claims, 2 Drawing Sheets

U.S. PATENT DOCUMENTS 6,537,240 B1 * 3/2003 Cavicchioli et al. ....... 604/5.01
6,582,656 B1 * 6/2003 Steuer et al. ................. 422/44

FOREIGN PATENT DOCUMENTS

WO     WO 98/17334     4/1998

\* cited by examiner

DEVICE AND A METHOD FOR DETERMINING BLOOD RECIRCULATION IN A VASCULAR ACCESS

BACKGROUND OF THE INVENTION

The present invention relates to a device and a method for determining blood recirculation in a vascular access.

The efficiency of a dialysis treatment is defined as the ratio of the volume of blood purified from by-products of the metabolism (urea, creatinin, etc.) during the dialysis session to the patient's total blood volume.

A simplified model of the blood flows that occur when an extracorporeal blood circuit is connected to the vascular system of a patient through a corporeal access of the type of a Cimino-Brescia fistula is shown in FIG. 1, in which 1 denotes the heart, 2 denotes the pulmonary circuit, 3 denotes the vascular system (or systemic circuit) and 4 denotes a dialyzer, connected to the systemic circuit 3 via an inlet line 5 (arterial line) and an outlet line 6 (venous line).

As can be seen from FIG. 1, the blood treated in the course of a dialysis session comes from the systemic circuit 3, in which the blood flows at a limited flow rate; therefore existing dialysis treatments have an intrinsically rather low dialytic efficiency and at present there are no corrective measures by which its value can be increased.

Moreover, the efficiency of a dialysis treatment is further reduced by the phenomenon known in medical circles as recirculation in the vascular access: on account of a number of factors such as the flow rate of blood circulating in the extracorporeal circuit, the position of the needles and the degree of stenosis of the fistula, a portion of the blood circuit which is returned, after the dialysis treatment, into the patient's body via the venous line 6, immediately re-enters the extracorporeal circuit via the arterial line 5, as shown in the detail in FIG. 2. FIG. 2 represents a vascular access (fistula), in which the needles for withdrawal and re-admission of the blood are denoted by 7 and 8.

The value $A_R$ of recirculation in the vascular access is generally defined by the following equation:

$$A_R\% = \frac{Q_R}{Q_B} \cdot 100 \qquad (1)$$

in which $Q_B$ is the blood flow circulating in the extracorporeal circuit and $Q_R$ is the blood flow returning to the extracorporeal circuit via the arterial line 5 immediately after dialysis treatment.

Knowledge of the value $A_R$ of recirculation in the vascular access is of considerable importance in dialysis treatments for many reasons, such as the repositioning of the needles 7, 8 when the value $A_R$ of the recirculation becomes too high, increase in accuracy of dialysis treatment, long-term monitoring of the stenosis of the fistula and increase in average life of the fistula.

For determination of the value $A_R$ of recirculation in the vascular access, numerous methods of measurement are known, which can be placed in two broad groups, the first comprising non-provocative methods of measurement and the second comprising the provocative methods of measurement.

The first group includes methods of measurement that do not involve chemical or physical stressing of the blood undergoing dialysis treatment but are limited to quantifying physiological values in the course of the dialysis session.

For example, this first group includes the method of measurement "with urea samples", which involves measuring the concentration of urea in three blood samples taken simultaneously in the arterial line, in the venous line and the patient's peripheral circuit, and calculating the value $A_R$ of recirculation in the vascular access according to the equation (equivalent to 1):

$$A_R\% = \frac{C_S - C_A}{C_S - C_T} \cdot 100 \qquad (2)$$

in which $C_S$ is the value of the urea concentration in the peripheral circulation (systemic concentration), $C_A$ is the value of the urea concentration in the arterial line (arterial concentration), and $C_V$ is the value of the urea concentration in the venous line (venous concentration).

However, this method has the drawback of being based on the basic assumption that, in the absence of recirculation in the vascular access, the value of the systemic concentration $C_S$ is equal to the value of the arterial concentration $C_A$; it has recently been demonstrated, however, that this assumption is not valid in all conditions and depends on the collection point, therefore even in the absence of recirculation in the vascular access there are differences between these values, which prejudices the reliability of the measurement.

On the other hand, the second group includes methods of measurement involving chemical or physical stressing of the blood undergoing the dialysis treatment.

This second group includes for example the method of measurement "with urea samples and minimum $Q_B$" which is substantially identical to the method of measurement "with urea samples" described above, differing from it in that blood sampling in the arterial line for determining the value $C_S$ of the systemic concentration is effected in conditions of minimum circulating blood flow $Q_B$ in the extracorporeal circuit, so as to minimize recirculation in the fistula and hence reduce the differences between the values $C_S$ and $C_A$ of systemic concentration and arterial concentration.

The second group also includes methods of measurement "in dilution" which envisage administration of a tracer to the patient, in order to obtain blood dilution of a chemical and physical character, and simultaneous monitoring, by means of special sensors, of its behaviour with respect to one or both of the arterial and venous lines. By comparing the signals detected by the sensors it is possible to determine, in a known manner which is therefore not described in detail, the value $A_R$ of recirculation in the vascular access.

In particular, a first known method of measurement in dilution envisages measurement of blood temperature by temperature sensors arranged on the venous line and on the arterial line for monitoring the variation of the respective temperatures in response to a quantity of heat (tracer) administered to or extracted from the blood by means of the dialysis machine.

A second known method of measurement in dilution is described in U.S. Pat. No. 5,312,550 and envisages injection, in the venous line, of a material possessing physical properties different from those of the blood and detection of the condition of recirculation in the vascular access by monitoring the presence of the physical properties of the material upstream from the point of injection of the material.

A third known method of measurement in dilution is described in U.S. Pat. No. 5,510,717 and envisages measurement of conductivity of the blood using a bolus of hypertonic solution injected in the venous line as "tracer" and two conductivity sensors provided on the venous line and on the arterial line for monitoring the variations of the respective conductivity in response to the aforesaid bolus.

A fourth known method of measurement in dilution envisages measurement of blood density using a bolus of isotonic physiological solution injected in the venous line as tracer and two conductivity sensors provided on the venous line and on the arterial line for monitoring the variation of the respective blood densities in response to the aforesaid bolus.

A fifth known method of measurement in dilution envisages measurement of optical absorbency of the blood using a single sensor of dilution of the blood (haematocrit measuring device) provided on the arterial line and, as tracer, a bolus of isotonic solution injected upstream from the sensor; the value $A_R$ of recirculation in the vascular access is found by comparing the signal detected by the sensor immediately after injection of the bolus and that observed after the bolus has entered the arterial access.

The provocative and non-provocative methods described above have some drawbacks, however, which have not permitted sufficient and complete exploitation of their merits. In particular, the non-provocative methods are difficult to execute as they require blood samples and laboratory tests, while the provocative methods, as well as being of the invasive type, are imprecise in time and breadth as they require manual injections and can in certain situations be altered by external effects.

Another drawback that is common to all the provocative methods described above is that determination of recirculation in the vascular access is effected by inducing a disturbance in the patient's blood that is of a finite extent and duration, and then calculating the value of recirculation only when the system is in a steady state, i.e. only after the disturbance induced in the patient's blood has passed through the patient's body and has been able to generate an induced disturbance at the point where the measurement sensors are located.

This characteristic that is common to the known methods on the one hand does not permit the execution of continuous monitoring of recirculation in the vascular access but only monitoring at discrete intervals of time that are spaced relatively far apart, and on the other hand does not permit reliable monitoring of the efficiency of the dialysis filter and timely intervention in situations of malfunction of the dialysis machine.

Moreover, in order to obtain an acceptable overall accuracy of measurement of recirculation in the vascular access it is necessary for the signals generated by the measurement sensors to be of sufficient amplitude to provide signal/noise ratios such as guarantee attainment of the accuracy. However, the finite duration of the induced disturbance has the effect that to obtain such amplitudes it is necessary to induce disturbances in the patient's blood that have relatively high amplitudes, which might cause undesirable changes in the dialysis treatment that could, in some particular clinical conditions, be harmful to the organism.

To remedy some of the drawbacks inherent to the known methods, Italian patent IT 1288767 describes a method of measurement that envisages using a provocative measurement performed by varying the ultrafiltration flow in the dialysis filter, without administering a tracer. In detail, the method envisages controlling the variation of ultrafiltration flow of the blood flowing inside the dialysis filter in the course of the dialysis session so as to produce a variation in the concentration of haemoglobin in the blood of a finite extent and duration, then measuring, by means of a haemoglobinometer, the variation in haemoglobin concentration that is induced upstream from the dialysis filter after the blood with altered haemoglobin concentration has been returned to the patient's body, and determining the value of recirculation in the vascular access on the basis of the measured change in haemoglobin concentration.

The method that is the object of the Italian patent cited above, though being particularly advantageous both from the standpoint of simplicity of implementation, as it does not require modifications of the dialysis machine and, using just one sensor, has greatly reduced measurement errors, and from the standpoint of simplicity of execution because, in addition to being of the non-invasive type, can be executed completely automatically without requiring the external interventions of an operator for the administration of a bolus of physiological solutions, still suffers the limitations resulting from determination of recirculation carried out in stationary conditions.

BRIEF SUMMARY OF THE INVENTION

The purpose of the present invention is to provide a device and a method for determining blood recirculation in a vascular access that makes it possible to overcome the limitations of the methods described above.

According to the invention, a method for determining blood recirculation in a vascular access of a patient undergoing a dialysis treatment by means of a dialysis machine comprising a collecting line for withdrawing blood from the patient's body, a dialysis filter, and a return line for returning blood into the patient's body, the recirculation taking place in the vascular access between the return line and the collecting line, is characterized in that it comprises the steps of:

inducing, in the blood flowing in the return line (26), a disturbance of a magnitude such as to bring the system into a transient state; and determining blood recirculation in the vascular access (11) during the transient state as a function of the magnitude of the disturbance induced in the collecting line (24).

For a better understanding of the present invention, a preferred embodiment is now described, purely as a non-limitative example, referring to the appended drawings, in which:

DETAILED DESCRIPTION OF THE INVENTION

Figure 1:
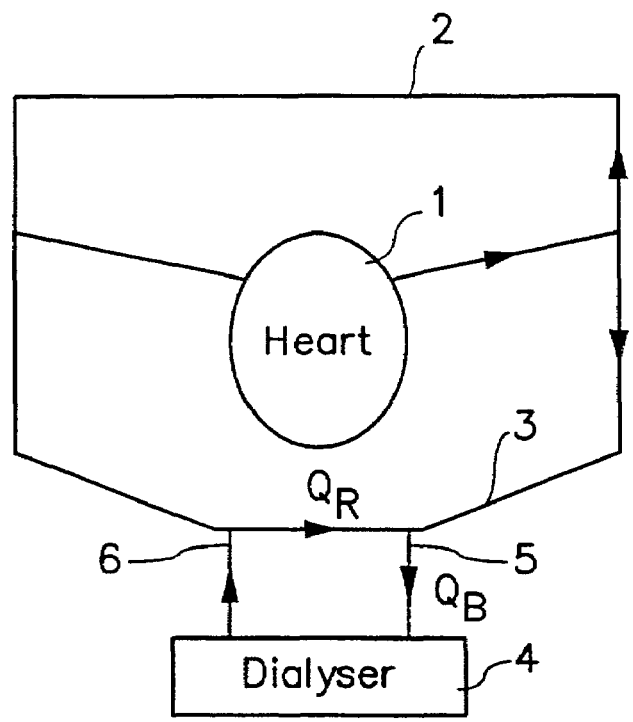
FIG. 1 shows a simplified model of the blood flows present in a patient's body in the presence of extracorporeal recirculation.
Figure 2:
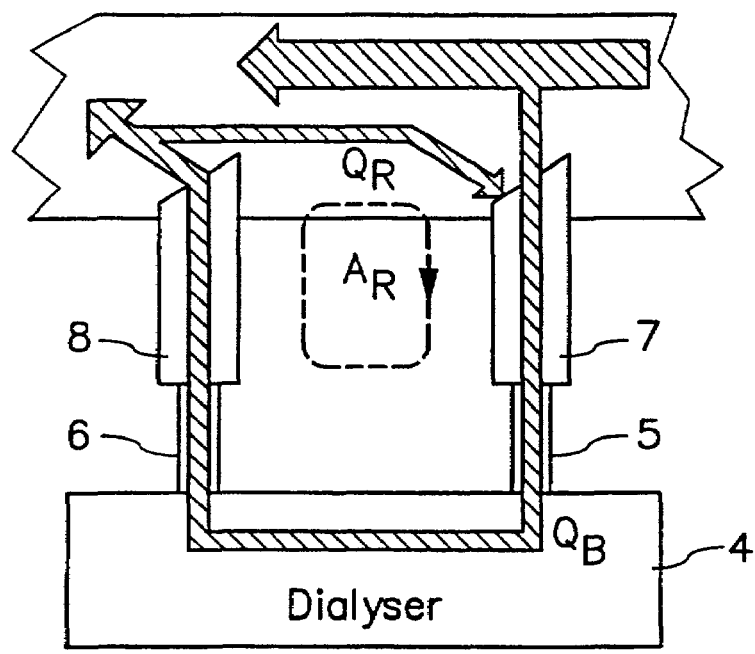
FIG. 2 is a simplified diagram of a vascular access and of the associated blood flows.
Figure 3:
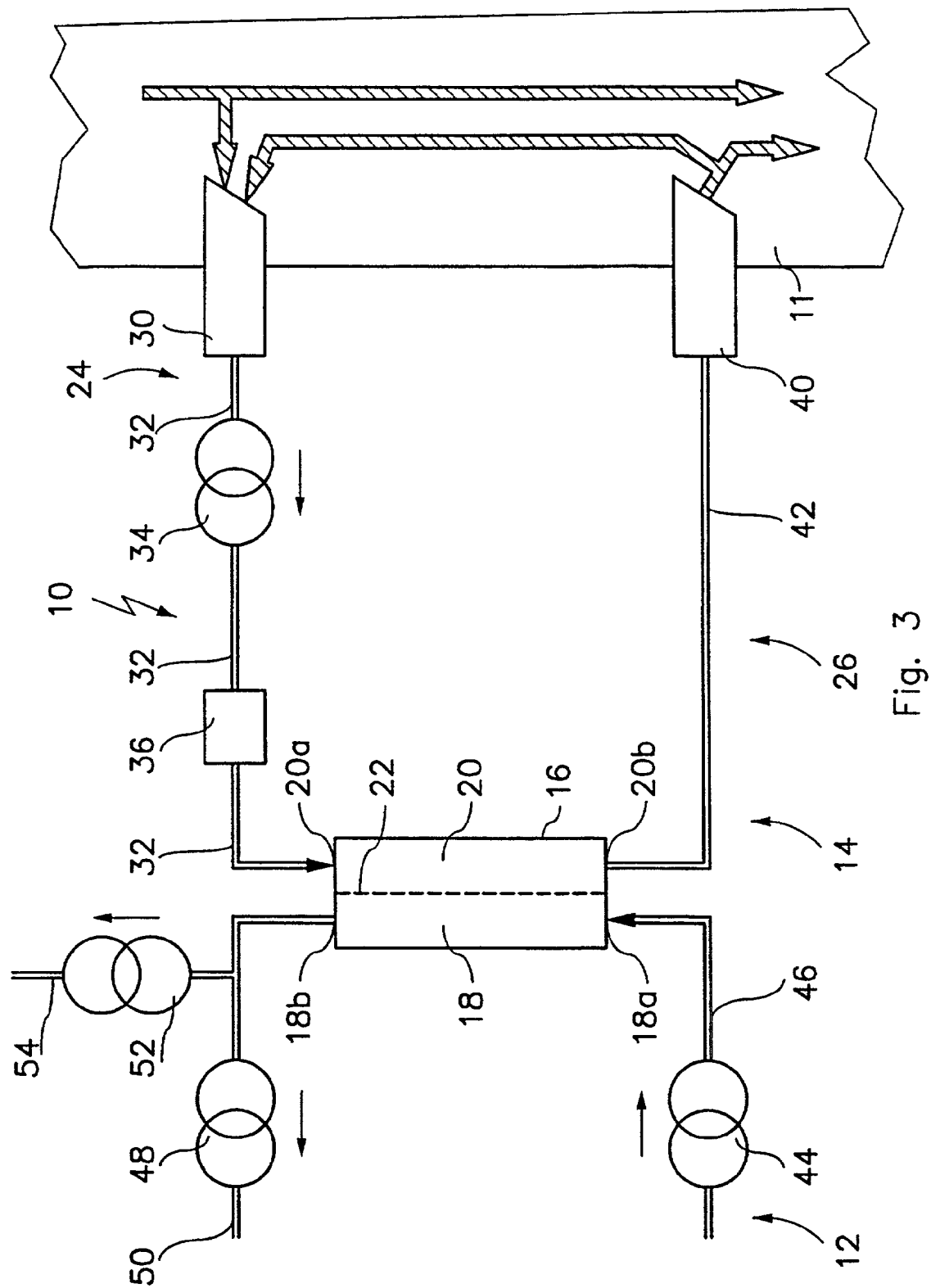
FIG. 3 is a simplified diagram of a dialysis machine.

In FIG. 3, the reference numeral 10 indicates a dialysis machine connected to a fistula 11 (vascular access) of a patient undergoing dialysis treatment. In FIG. 3, the dialysis machine 10 is shown in relation to the only parts that are necessary for understanding the device and the method to which the present invention relates, and this diagram also indicates the blood flows in the vascular access.

The dialysis machine 10 comprises a dialysis solution line 12 through which a dialysis solution passes when in use, and which is made up of a number of sections; a blood line 14 through which the blood of the patient undergoing dialysis treatment passes when in use, it too comprising a number of sections; and a dialysis filter 16 for purifying the blood, connected to the dialysis solution line 12 and to the blood line 14 in the manner described below.

In particular, the dialysis filter 16 comprises a dialysis liquid compartment 18 inside which the dialysis solution flows when in use, arranged along the dialysis solution line 12 and having an inlet 18a and an outlet 18b connected to the dialysis solution line 12; a blood compartment 20 inside which the blood to be purified flows, when in use, arranged along the blood line 14 and having an inlet 20a and an outlet 20b connected to the blood line 14; and a semi-permeable membrane 22, i.e. permeable to blood plasma and to the undesirable substances of low molecular weight present in the blood on account of renal insufficiency, which separates the dialysis liquid compartment 18 and the blood compartment 20.

Blood line 14 comprises an arterial inlet line 24 connected between the inlet 20a of the blood compartment 20 and the fistula 11 of the patient and a venous outlet line 26 connected between the outlet 20b of the blood compartment 20 and the fistula 11 downstream from the arterial line 24 (relative to the direction of blood flow in fistula 11).

Arterial line 24 comprises a first needle 30 inserted in the fistula 11 of the patient and connected to the inlet 20a of blood compartment 20 via an inlet duct 32, a blood pump 34 arranged along the inlet duct 32, the flow rate (delivery) of which determines the volume of blood submitted to dialysis treatment, and a haemoconcentration sensor 36 (haemoglobinometer) also arranged along the inlet duct 32 and supplying a haemoconcentration signal at its output.

Venous line 26 comprises a second needle 40 inserted in fistula 11 of the patient downstream from the first needle 30, and a predetermined distance from the latter, and connected to the outlet 20b of blood compartment 20 via an outlet duct 42.

The dialysis solution line 12 comprises an inlet dialysate pump 44 connected to the inlet 18a of dialyser compartment 18 via an inlet duct 46, an outlet dialysate pump 48 connected to the outlet 18b of dialyser compartment 18 via an outlet duct 50, and an ultrafiltration pump 52 arranged on a shunt line 54 connected to outlet duct 50 and having the purpose of regulating the value $Q_{UF}$ of the ultrafiltration flow in the dialysis filter 16.

The present invention is based on the principle of carrying out a non-invasive provocative measurement, i.e. without administration of tracer, working with the system in dynamic or transient conditions.

In particular, the present invention envisages:

submitting the patient's blood flowing in blood line 10 to stressing of a physical nature consisting of one or more temporally successive disturbances being of a magnitude such as to bring the system into transient conditions; and determining the recirculation of blood in the vascular access when the system is in the transient conditions in relation to the magnitude of the disturbances present in the blood line 10, upstream from the point at which the blood was submitted to the aforementioned physical stressing, and induced by the recirculation of blood in the vascular access.

In particular, according to one aspect of the present invention, the aforementioned stressing of a physical nature consists in a continuous variation of the haemoglobin concentration of the blood flowing in venous line 26 around a predetermined average value or around a predetermined concentration profile more suitable for the patient and calculation of recirculation in the vascular access is performed during the transient conditions produced by the variation, in relation to the variation in haemoglobin concentration induced in the blood flowing in arterial line 24, which can be measured by means of the haemoconcentration sensor 36.

According to a preferred embodiment of the present invention, the variation of the haemoglobin concentration in the blood flowing in venous line 26 is obtained by generating continuous variations of the ultrafiltration flow in dialysis filter 16, which are obtained by suitably controlling the ultrafiltration pump 52.

In particular, ultrafiltration pump 52 is operated in such a way that the value of the ultrafiltration flow has a succession of positive steps (increase in ultrafiltration flow) and negative steps (decrease in ultrafiltration flow) of a value that correlates with the magnitude of the disturbance that is to be created; the positive steps cause an increase in haemoglobin concentration in the blood flowing in venous line 26, which is readmitted into fistula 11 of the patient via needle 40, whereas the negative steps cause a decrease in the concentration.

At each change produced in the haemoglobin concentration of the blood, i.e. after each step of ultrafiltration flow, while the system is in a transient state caused by the step, the haemoglobin concentration of the blood flowing in arterial line 24 is determined by means of haemoconcentration sensor 36 and hence, on the basis of a series of values assumed by the haemoglobin concentration within a predetermined time window, the recirculation of blood in the vascular access is then calculated, using a mathematical algorithm.

In particular, at predetermined time intervals, for example every second, a change of a known amount is caused in the haemoglobin concentration of the blood in venous line 26 and at the same instant the haemoglobin concentration of the blood in arterial line 24 is measured.

The pair of values of the haemoglobin concentration in the venous line and in the arterial line is then inserted in a vector containing other pairs of corresponding values acquired in previous time intervals and the vector thus formed is then processed using the aforementioned calculation algorithm so as to estimate the value of blood recirculation in the vascular access, minimizing the estimation error.

One of the most suitable mathematical algorithms that can be used for calculating the recirculation in the vascular access is based on modeling of the behaviour of the system comprising the blood and the lines in which it is circulating, the modeling being effected using a first-order linear model and the method of least squares based on algebraic operations effected on matrices whose dimensions coincide with the number of parameters of the mathematical model that have to be estimated and the number of pairs of values considered (for example with 4 parameters to be estimated and sixty pairs of values—the number of pairs acquired in one minute—matrices having the dimensions 4×60 are generated).

In particular, a first-order linear modeling of the system is equivalent to writing a differential equation, the characteristic parameters of which can be estimated by stimulating the system with a variable input signal and measuring its output.

This can be done in various ways. There now follows a synoptic description of one possible approach, without any loss of generality.

Considering the input and output of the system only at finite moments of time, the differential equation describing the system, whatever it is, assumes the following discrete form:

$$y(i+1) = a \cdot y(i) + b \cdot u(i-n) + c$$

in which:
y is the concentration of haemoglobin;
u is the ultrafiltration flow;
Tc is the sampling time; and
n=T/Tc is the delay in propagation of the disturbance, expressed in sampling periods; and
a, b and c are parameters that depend on the value of recirculation in the vascular access.

After a temporal displacement of n samples of the input signal (time window), the preceding discrete differential equation can be rewritten as follows:

$$\bar{u}(i) = u(i-n)$$

$$y(i+1) = a \cdot y(i) + b \cdot \bar{u}(i) + c$$

Applying a sequence of m input signals to the system and measuring the corresponding m output signals, the foregoing equations can be applied repeatedly for each input signal and, also considering the errors (that are to be minimized), for each of them we can in general write:

$$z(i+1) = a \cdot z(i) + b \cdot \bar{u}(i) + c + err(i)$$

or, in matrix form:

$$Z = H \cdot P + E$$

in which:

$$Z = \begin{bmatrix} z(1) \\ z(2) \\ \ldots \\ \ldots \\ z(m) \end{bmatrix};$$

$$H = \begin{bmatrix} z(0) & \bar{u}(0) & 1 \\ z(1) & \bar{u}(1) & 1 \\ \ldots & \ldots & \ldots \\ \ldots & \ldots & \ldots \\ z(m-1) & \bar{u}(m-1) & 1 \end{bmatrix};$$

$$P = \begin{bmatrix} a \\ b \\ c \end{bmatrix};$$

$$E = \begin{bmatrix} err(1) \\ err(2) \\ \ldots \\ \ldots \\ err(m-1) \end{bmatrix}$$

Applying the method of least squares, it can easily be demonstrated that matrix P that minimizes the errors is as follows:

$$P = (H' \cdot H)^{-1} \cdot H' \cdot Z$$

A measure of the quality of the estimate can be given by the variance of the error, which has the following expression:

$$\sigma^2 = \frac{(Z - H \cdot P)^{-1} \cdot (Z - H \cdot P)}{m - 3}$$

On the basis of the foregoing, the value $A_R$ of recirculation in the vascular access can then be calculated on the basis of the estimated parameters a, b and c.

The advantages of the present method of measurement are as follows.

Firstly, the present method envisages inducing, in the patient's blood, a continuous disturbance whose duration is equal to the duration of the dialysis treatment, thus permitting continuous monitoring of recirculation in the vascular access and of the efficiency of the dialysis filter and therefore timely intervention if there are malfunctions of the dialysis machine.

In addition, the continuity of the disturbance induced in the patient's blood makes it possible to obtain high accuracy of measurement of recirculation in the vascular access without in any way adversely affecting the dialysis treatment and the clinical objective of the dialysis session, and thus without repercussions on the patient's body, since the disturbance that is induced causes a continuous variation of the haemoglobin concentration around an average value or around a predetermined concentration profile that is suitable for the patient.

Moreover, knowledge of the recirculation in the vascular access in real time makes it possible to pursue the clinical objectives more accurately.

Thus, during the dialysis session, typically the haemoglobin concentration, and the variation in haematic volume that is derived therefrom, are modified according to a profile that is suitable for the patient, and modification is made on the basis of information on the haemoglobin concentration supplied by the haemoconcentration sensor 36.

Since, however, the recirculation in the vascular access also makes a contribution to the variation of the haemoglobin concentration, the haemoglobin concentration measured by the haemoconcentration sensor 36 is generally the combination of the two aforesaid contributions and therefore knowledge in real time of the magnitude of recirculation in the vascular access proves to be extremely important in that it makes it possible to make real-time corrections to the command fed to the dialysis machine so that the desired profile of haemoglobin concentration can be followed more accurately.

Furthermore, the present method is simple in implementation as it requires neither blood samples and laboratory tests, nor manual injections, and can be carried out completely automatically as there is no need for external interventions by an operator for administering a bolus of physiological solution.

Moreover, the method requires just one sensor, the haemoglobinometer, instead of two as in many of the known methods described above, and therefore permits further reduction of the measurement errors.

Finally, the method is simple, it is easy to implement and does not require any modifications of the dialysis machine, since the haemoglobinometer and the ultrafiltration pump are already present in ordinary dialysis machines.

Finally, it is clear that the method described and illustrated here can be modified and varied without leaving the scope of protection of the present invention.

For example, variation of the haemoglobin concentration can instead be obtained by continuously varying the ultrafiltration flow, i.e. by continuously varying the quantity of water extracted from the blood, or by varying the infusion flow, i.e. by continuously varying the quantity of water infused into the blood.

Moreover, although variation of the haemoglobin concentration of the blood is the most convenient disturbance to use, other types of disturbances can be employed, among which we may mention, for example, variation of the temperature of the blood.

The invention claimed is:

1. A method for determining blood recirculation comprising:
    withdrawing blood from a body of a patient through a withdrawal line;
    returning blood into the patient's body through a return line;
    inducing a succession of variations of value of a blood parameter in the blood flowing in the return line, each of the variations comprising an increase and a decrease of said value of said blood parameter around an average value or around a predetermined profile;
    measuring, for each of the variations, at least one value of said blood parameter of the blood flowing in the withdrawal line; and
    determining a blood recirculation value in a vascular access of the patient between the return line and the withdrawal line, as a function of said blood parameter values measured for at least one variation and for temporally preceding variations of value of the blood parameter in the blood flowing in the return line.

2. A method according to claim 1, wherein said blood parameter is one of hemoglobin concentration and blood temperature.

3. A method according to claim 1, wherein said succession of variations is induced by varying at least one of:
    an ultrafiltration flow ultrafiltered from the extracorporeal blood; and
    an infusion flow infused into the extracorporeal blood.

4. A method according to claim 1, further comprising acquiring, for each variation, at least one value indicative of said blood parameter of the blood flowing in the return line; the blood recirculation value being determined as a function of values indicative of said blood parameter of the blood flowing in the return line acquired for at least one variation and for temporally preceding variations.

5. A method according to claim 1, wherein the blood recirculation value is calculated by means of a linear first order model, said first order model having parameters estimated using a method of least squares.

6. A method according to claim 1, wherein said succession of variations is continuous.

* * * * *

UNITED STATES PATENT AND TRADEMARK OFFICE
CERTIFICATE OF CORRECTION

PATENT NO. : 7,001,353 B2
DATED : February 21, 2006
INVENTOR(S) : Antonio Bosetto et al.

It is certified that error appears in the above-identified patent and that said Letters Patent is hereby corrected as shown below:

<u>Title page,</u>
Item [75], Inventors, insert -- Massimo Fava, Mirandola (IT) --.

Signed and Sealed this

Twenty-fifth Day of April, 2006

JON W. DUDAS
*Director of the United States Patent and Trademark Office*